Figure 1:
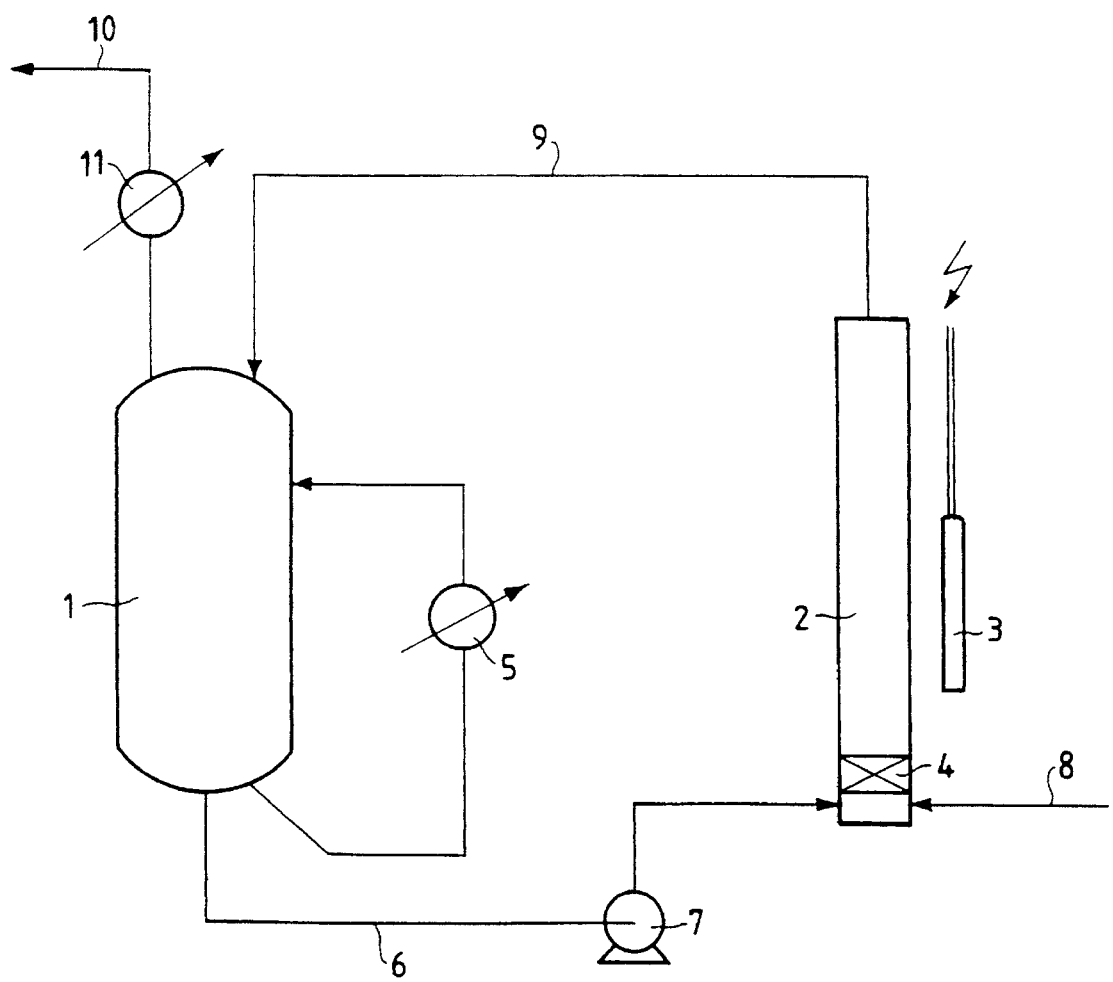

United States Patent
Ribaldo et al.

[11] Patent Number: 5,514,254
[45] Date of Patent: May 7, 1996

[54] PROCEDURE FOR THE PHOTOCHLORINATION OF ALKYL-AROMATIC COMPOUNDS

[75] Inventors: Carlo Ribaldo; Giuseppe Contardi; Vittorio Messori, all of Milan, Italy

[73] Assignee: Enichem Synthesis S.p.A., Palermo, Italy

[21] Appl. No.: 198,576

[22] Filed: Feb. 18, 1994

[30] Foreign Application Priority Data

Feb. 24, 1993 [IT] Italy .................. MI93A0346

[51] Int. Cl.⁶ .................................. C07C 17/00
[52] U.S. Cl. .................. 204/157.6; 204/157.65; 204/157.94; 204/157.99; 204/158.1
[58] Field of Search ............ 204/157.6, 157.65, 204/157.94, 157.99, 158.1

[56] References Cited

U.S. PATENT DOCUMENTS

| | | | |
|---|---|---|---|
| 3,392,098 | 7/1968 | Restaino | 204/163 |
| 4,056,455 | 11/1977 | Lademann et al. | 204/163 R |
| 4,268,457 | 5/1981 | Colson et al. | 260/544 P |
| 4,331,821 | 5/1982 | Schubart et al. | 570/196 |
| 4,348,265 | 9/1982 | Strom | 204/158 HA |
| 4,643,811 | 2/1987 | Langlois | 204/157.8 |
| 4,689,425 | 8/1987 | Kachhy et al. | 560/103 |
| 5,279,719 | 1/1994 | Sunagawa et al. | 204/157.6 |

FOREIGN PATENT DOCUMENTS

| | | |
|---|---|---|
| 2530094 | 11/1976 | Germany . |
| 3320020 | 12/1983 | Germany . |
| 928693 | 5/1960 | United Kingdom . |

Primary Examiner—T. Tung
Assistant Examiner—C. Delacroix-Muirheid
Attorney, Agent, or Firm—Oblon, Spivak, McClelland, Maier & Neustadt

[57] ABSTRACT

An alkyl-aromatic compound is selectively photochlorinated in the side chain in a cyclic reaction system wherein said compound is continuously circulated between a container and photochlorination reactor.

The compound is partially chlorinated after each passage through the photochlorination reactor, the number of passages depending on the degree of chlorination required.

The procedure is particularly useful for the preparation of benzyl chloride, benzal chloride and benzotrichloride, and the corresponding halogen-substituted derivatives of the nucleus.

14 Claims, 1 Drawing Sheet

PROCEDURE FOR THE PHOTOCHLORINATION OF ALKYL-AROMATIC COMPOUNDS

The present invention relates to a procedure for the selective photochlorination in the side chain of alkyl-aromatic compounds.

It is known that the chlorination in the side chain of alkyl-aromatic compounds is generally favored by raising the reaction temperature or, more commonly, by operating in the presence of free radical initiators such as light radiation or peroxides.

Particularly known in the art is the chlorination in the side chain of toluene, and its chlorine-substituted derivatives in the nucleus, to benzyl chloride, benzal chloride and benzotrichloride. These compounds are useful intermediates which can be transformed into other chemical products, especially by reactions involving chlorine substituents in the side chain. In this way benzyl chloride can be used in the production of benzyl butyl phthalate, a plasticizer for vinylic resins, benzal chloride can be hydrolyzed to benzaldehyde and benzotrichloride can be transformed into benzoyl chloride. In addition also some chlorine-substituted derivatives in the nucleus of the above compounds have a commercial value; for example p-chlorobenzotrichloride is an important intermediate in the production of dinitroaniline weed-killers.

The basic problem related to procedures for the thermal and photochemical chlorination of alkyl-aromatic compounds consists in the limited selectivity of the desired reaction product. For example in the production of benzyl chloride there is normally only a partial conversion of the toluene, in order to minimize the formation of products with a degree of chlorination which is higher than that required. The same happens in the production of benzal chloride. Finally in the preparation of benzotrichloride, the product with a higher degree of chlorination in the side chain, the selectivity of the reaction is reduced by the presence of by-products. All of this involves difficult operations for the separation and purification of the useful products and for recycling the unaltered reagents.

With respect to the known photochlorination methods of organic compounds, either batch or continuous, basically two types of reactors are used and more specifically: a vessel reactor with one or more immersed lamps and a film reactor with an internal lamp. In the traditional vessel reactors the stirring which is necessary to allow the chlorine to flow near the lamps and the organic compound to be effectively exchanged, is provided by bubbling the chlorine itself and hydrochloric acid which is developed as a reaction by-product. This causes a limited feeding flexibility of the chlorine which can be partially remedied by connecting several reactors to each other in series, mainly to use up as much chlorine as possible discharged from the photochlorination. In the film reactor, this problem does not exist, but as the process is carried out in the presence of a radiated gaseous phase, the use of these reactors in photochlorination is restricted to cases where the chlorine does not form an explosive mixture with the organic compound to be chlorinated. Other problems related to photochlorination methods of the known art consist in the difficulties of thermal exchange, in that the heat of the reaction is only exchanged through the reactor jacket; the difficulty of regulating the temperature and the ratio between chlorine and aromatic compound during the reaction; the dirtying of the lamp immersed in the reaction mixture; the limited operating pressures due to the glass seal of the lamp-holder; and the difficulty in providing a system which completely satisfies security regulations.

The purpose of the present invention is to overcome the disadvantages of the known art related to procedures for the photochemical chlorination of alkyl-aromatic compounds.

In particular it has been found, in accordance with the present invention, that it is possible to photochlorinate alkyl-aromatic compounds with practically total conversions of the reagents and with a high selectivity in the useful reaction product, operating with a batch circulation system with the progressive chlorination of the alkyl-aromatic compound. It has also been found that this photochlorination system is extremely safe and suitable for overcoming the disadvantages and limitations of the known art mentioned above.

In accordance with this the present invention relates to a procedure for the selective photochlorination in the side chain of an alkyl-aromatic compound by contact with chlorine under the action of light radiation, characterized in that:

said alkyl-aromatic compound is continuously removed from a container, mixed with chlorine in a static mixer, to obtain a homogeneous mixture, which is fed to the foot of a tubular-shaped reactor, without any mechanical stirring equipment, at least partially composed of material which is transparent at light radiation and externally equipped with a supply of light radiation, said reactor being maintained under photochlorination conditions, to almost completely use up the chlorine, and recover a mixture of the chlorinated alkyl-aromatic compound and hydrochloric acid by-product at the head of the reactor, said reaction mixture being continuously recycled to the container where the gaseous hydrochloric acid is separated from the chlorinated alkyl-aromatic compound, the alkyl-aromatic compound being partially chlorinated at each recycling in the reactor, the number of recycles depending on the degree of chlorination required.

The alkyl-aromatic compounds which can be subjected to the photochlorination process of the present invention are preferably toluene, monochlorotoluene isomers, dichlorotoluene isomers trichlorotoluene, xylene isomers and mesitylene. The photochlorination products are those which are mono or polychlorinated in the side chain. For example in the case of toluene, benzyl chloride, benzal chloride or benzotrichloride can be obtained, depending on the reaction conditions.

According to an embodiment of the present invention, the alkyl-aromatic compound is removed from a container and fed to the photochlorination reactor by a suitable pump, after mixing with chlorine and homogenizing the mixture by passing it through a static mixer. In this phase of the procedure the ratio between chlorine and the alkyl-aromatic compound is such that the chlorine, or a substantial quantity of this, is dissolved in the liquid phase at the inlet of the photochlorination reactor. Suitable concentrations of chlorine generally vary from 0.02 to 2 and preferably from 0.1 to 1 parts by weight for every 100 parts by weight of the alkyl-aromatic compound.

The photochlorination reactor used in the present invention is generally a long, tubular shaped reactor, for example with a ratio between length and diameter of about 50/1, without any stirring devices and composed of a material which is transparent at light radiation or having one or more windows which are permeable to said radiation. At least one source of light radiation is placed outside the reactor in a suitable position, and the light is either a visible or an UV radiation, for example with a wave-length of 150–600 nm and preferably 300–400 nm. Sources of radiation normally used are mercury arc lamps (with high, medium or low pressure), or xenon lamps, which emit in a UV/visible range. These devices are available on the market.

In the photochlorination reactor the linear rate of the mixture varies from 0.4 to 4 meters/second and preferably from about 0.5–2 meters/second, with an inlet temperature ranging from 0° to 150° C. and maintaining a difference of temperature between the outlet and inlet at values of 1° to 35° C. The inlet temperature of the mixture is conveniently regulated by means of a heat exchanger.

Operating under these conditions the chlorine is completely or almost completely used up and the reaction mixture is sent to the container where the hydrochloric acid, a reaction by-product, is separated from the liquid phase.

The alkyl-aromatic compound is then subjected to progressive chlorination, the number of recycles depending on the desired degree of chlorination.

The procedure of the present invention has the following effects and advantages:

- the means of feeding the reagent mixture to the photochlorination reactor ensure excellent fluodinamic conditions in the reactor, regardless of the quantity of chlorine fed;
- the source of radiation external to the reactor and the fact that the chlorine is dissolved or at least uniformly dispersed in the liquid phase enable the operation to be carried out without hot points, thus avoiding the formation of explosive mixtures which are typical in the gaseous phase;
- the possibility of independently regulating the feeding of the chlorine and the reaction temperature, makes it possible to operate under excellent conditions in relation to the depletion of the chlorine and selectivity of the reaction product desired, with a practically complete conversion of the alkyl-aromatic compound subjected to photochlorination;
- there is no limitation relating to the thermal exchange as the temperature of the reagent mixture can be regulated to the most suitable value for the particular reaction, with the consequent possibility of exploiting the fast kinetics to the utmost;
- there are no problems of the radiation lamps being dirtied thus facilitating maintenance operations;
- finally there are no limitations deriving from the operating pressures.

FIG. 1 of the enclosed drawing schematically shows suitable equipment for the embodiment of the procedure of the present invention.

In particular this figure shows with (1) a container of the alkyl-aromatic compound subjected to chlorination and with (2) the photochemical reactor, having a long tubular shape, made of material which is transparent to light radiation, at least in the part next to the source (3) of light radiation. The alkyl-aromatic compound subjected to chlorination is continuously removed from the container (1) by means of line (6) and fed, through the pump (7) to the bottom of the reactor (2). The chlorine is continuously fed through line (8) to the bottom of the reactor. The alkyl-aromatic compound and the chlorine are mixed and homogenized in the static mixer (4) and the homogeneous mixture is subjected to photochlorination conditions in the reactor (2). The reaction mixture composed of the chlorinated alkyl-aromatic compound and hydrochloric acid is removed from the head of the reactor (2) and sent to the container (1) by line (9). The hydrochloric acid is discharged from the reactor (1) through line (10), after passing through the exchanger (11). In the form of embodiment shown in FIG. 1, the exothermal effect of the reaction is controlled by continuously recirculating the contents of the container (1) through the exchanger (5). This exothermicity however can be controlled by the exchangers situated on line (6) and/or on line (9), instead of or in addition to exchanger (5).

A single photochlorination reactor (2) can be used or two or more reactors, placed in series or parallel to each other, thus improving the productivity of the system.

EXAMPLE 1

Preparation of p-chlorobenzotrichloride from p-chlorotoluene.

With reference to FIG. 1, 3,400 g of p-chlorotoluene treated to eliminate metallic and inorganic impurities are charged into container (1). The p-chlorotoluene is removed from container (1) and fed, by pump (7) to the bottom of the reactor (2), with a rate of 200 liters/hour. Chlorine is also fed through line (8) to the bottom of the reactor, with an average rate of 1,432.5 g/hour. The liquid and gaseous reagents are homogenized in the static mixer (4) and reacted in the reactor (2). This reactor has a long cylindrical shape (length 300 mm, diameter 14 mm) and is made of nickel, except for the areas near the lamp (3), which are made of DURANSO material which is transparent with radiation. Lamp (3) is a commercial Heraeus TQ 150 lamp, with a power of 150 Watt, which emits radiations having a wave-length within the range of 240–579 nm, and is situated at a distance of about 10 cm from the transparent wall of the reactor. The reaction products are sent, by line (9) from the reactor (2) to the container (1) where the liquid product is separated from the gaseous hydrochloric acid. The liquid flow is fed to the bottom of the reactor at a temperature of between 40° C. and 70° C. and the flow leaving the reactor is at a temperature of between 50° and 75° C.

The operation is carried out for a period of 4 hours feeding a total of 5,730 g of chlorine and 6,180 g of p-chlorobenzotrichloride are obtained with a 100% conversion of the p-chlorotoluene and a yield of p-chlorotoluene which is higher than 99.8%. The analysis of the reaction product is as follows:

p-chlorotoluene: absent p-chlorobenzotrichloride: 99.9% w/w p-chlorobenzalchloride: 0.1% w/w products chlorinated in the nucleus: absent

EXAMPLE 2

The same procedure is carried out as for example 1, charging 2,500 g of purified 2,4-dichlorotoluene into the container (1). During the first hour of the reaction, the liquid is circulated between the container (1) and reactor (2) with a rate of 200 liters/hour, whereas 1,119 g of chlorine are gradually and uniformly fed through line (8). The temperature at the inlet of the reactor is 60° C. and at the outlet 65° C., and 3,082 g of a chlorinated product are obtained having the following analysis:

2,4-dichlorotoluene:<0.1% w/w 2,4-dichlorobenzylchloride: 90% w/w 2,4-dichlorobenzalchloride: 10% w/w 2,4-dichlorobenzotrichloride: absent.

The reaction is continued for a further 2.5 hours circulating the liquid between the container (1) and reactor (2) with a rate of 200 liters/hour, feeding 1,058 g of chlorine gradually and uniformly. The temperature at the inlet of the reactor is 30° C. and at the outlet 32° C., and 3,595 g of a chlorinated product are obtained having the following analysis:

2,4-dichlorobenzylchloride: absent
2,4-dichlorobenzalchloride: 95% w/w
2,4-dichlorobenzotrichloride: 5% w/w The reaction is continued for a further 2.5 hours circulating the liquid between the container (1) and reactor (2) with a rate of 300 liters/hour, feeding 1,050 g of chlorine gradually and uniformly. The temperature at the inlet of the reactor is 120° C. and at the outlet 121° C., and 4,105 g of a chlorinated product are obtained having the following analysis:

2,4-dichlorobenzalchloride: 0.2% w/w
2,4-dichlorobenzotrichloride: 99.8% w/w
chlorinated products in the nucleus: absent.

We claim:

1. A process for the selective photochlorination of the side chain of an alkyl-aromatic compound by contact with chlorine under action of light radiation comprising:
   1) continuously removing a portion of an alkyl-aromatic compound from a container;
   2) mixing said alkyl-aromatic compound with chlorine in a static mixer to obtain a homogeneous mixture;
   3) feeding said homogenous mixture, in the liquid phase, to the bottom of a long-tubular-shaped reactor, without any mechanical stirring, said reactor being at least partially composed of a material which is transparent to light radiation and externally equipped with a supply of light radiation, said reactor being maintained under photochlorination conditions;
   4) reacting said homogenous mixture to almost completely use up said chlorine; and
   5) recovering a reaction mixture of a chlorinated alkyl-aromatic compound and hydrochloric acid by-product, at the head of said reactor,
   wherein said reaction mixture is continuously cycled to said container, where a gaseous hydrochloric acid is separated from said chlorinated alkyl-aromatic compound, and
   wherein said alkyl-aromatic compound is partially chlorinated at each cycling in said reactor, the number of cycles depending on the degree of chlorination desired.

2. The process according to claim 1, wherein said alkyl-aromatic compound is selected from toluene, monochlorotoluene isomers, dichlorotoluene isomers, xylene isomers and mesitylene.

3. The process according to claim 2, wherein said alkyl-aromatic compound is toluene.

4. The process according to claim 2, wherein said alkyl-aromatic compound is mesitylene.

5. The process according to claim 2, wherein said alkyl-aromatic compound is selected from monochlorotoluene isomers.

6. The process according to claim 2, wherein said alkyl-aromatic compound is selected from dichlorotoluene isomers.

7. The process according to claim 2, wherein said alkyl-aromatic compound is selected from xylene isomers.

8. The process according to claim 2, wherein said several photochlorination reactors are arranged in parallel.

9. The process according to claim 2, wherein said several photochlorination reactors are arranged in series.

10. The process according to claim 1, wherein a mixture containing from 0.02 to 2 parts by weight of chlorine for every 100 parts by weight of the alkyl-aromatic compound is fed in the liquid phase to the chlorination reactor.

11. The process according to claim 1, wherein in said photochlorination reactor the linear rate of the reaction mixture is from 0.4 to 4 meters/second, with a temperature at the inlet ranging from 0° to 150° C. and maintaining a difference of temperature between the inlet and outlet at values of 1° to 35° C.

12. The process according to claim 11, wherein in said photochlorination reactor the linear rate of the reaction mixture is from about 0.5 to 2 meters/second.

13. The process according to claim 1, wherein several photochlorination reactors are used, arranged in series or parallel to each other.

14. The process according to claim 1, wherein a mixture containing from 0.1 to 1 parts by weight of chlorine for every 100 parts by weight of the alkyl-aromatic compound is fed in the liquid phase to the chlorination reactor.

* * * * *